United States Patent
North et al.

(10) Patent No.: US 8,447,408 B2
(45) Date of Patent: *May 21, 2013

(54) NEUROSTIMULATION THERAPY MANIPULATION

(75) Inventors: Richard B. North, Baltimore, MD (US); Jeffrey M. Sieracki, Silver Spring, MD (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/087,885

(22) Filed: Apr. 15, 2011

(65) Prior Publication Data

US 2011/0196455 A1  Aug. 11, 2011

Related U.S. Application Data

(63) Continuation of application No. 11/735,140, filed on Apr. 13, 2007, now Pat. No. 7,933,655, which is a continuation of application No. 10/696,781, filed on Oct. 29, 2003, now Pat. No. 7,216,000.

(60) Provisional application No. 60/422,260, filed on Oct. 31, 2002, provisional application No. 60/503,214, filed on Sep. 15, 2003.

(51) Int. Cl.
*A61N 1/00* (2006.01)

(52) U.S. Cl.
USPC ............................................. 607/46; 607/59

(58) Field of Classification Search
USPC .......................... 607/43–48, 59, 62
See application file for complete search history.

(56) References Cited

U.S. PATENT DOCUMENTS

| 4,208,008 A | 6/1980 | Smith |
| 4,793,353 A | 12/1988 | Borkan |
| 5,615,318 A | 3/1997 | Matsuura |
| 5,938,690 A | 8/1999 | Law et al. |
| 5,983,140 A | 11/1999 | Smith et al. |
| 6,052,624 A | 4/2000 | Mann |
| 6,308,102 B1 | 10/2001 | Sieracki et al. |

(Continued)

FOREIGN PATENT DOCUMENTS

| WO | 0183028 | 8/2001 |
| WO | 2004041353 | 5/2004 |

OTHER PUBLICATIONS

Fowler, K.R., "Neurological Stimulation System", Proceedings AAMI 21st Annual Meeting, Apr. 12-16, 1986.

(Continued)

*Primary Examiner* — Scott Getzow
(74) *Attorney, Agent, or Firm* — Shumaker & Sieffert, P.A.

(57) ABSTRACT

A user, such as a clinician or the patient, uses a control device to manipulate at least one neurostimulation parameter. A mapping system uses a calibrated map to map the directional output of the control device to values of at least one stimulation parameter to allow the user to intuitively control the value of the parameter. In some embodiments, where a stimulation device is used to deliver spinal cord stimulation (SCS) therapy for example, the user manipulates a parameter to effect the location and/or strength of paresthesia experienced by the patient. In exemplary embodiments, the parameter values are combinations of electrodes, and the mapping system selects electrode combinations based on the output of the control device such that a direction of movement of paresthesia experienced by the patient corresponds to a direction of manipulation of a directional controller of the control device. The mapping system may calibrate the map based on patient paresthesia information received from a user.

23 Claims, 8 Drawing Sheets

U.S. PATENT DOCUMENTS

| | | | |
|---|---|---|---|
| 6,381,496 | B1 | 4/2002 | Meadows et al. |
| 6,393,325 | B1 | 5/2002 | Mann et al. |
| 6,587,724 | B2 | 7/2003 | Mann |
| 6,609,032 | B1 | 8/2003 | Woods et al. |
| 6,654,027 | B1 | 11/2003 | Hernandez |
| 6,659,968 | B1 | 12/2003 | McClure |
| 7,015,935 | B2 | 3/2006 | Herget et al. |
| 7,142,923 | B2 | 11/2006 | North et al. |
| 7,146,219 | B2 | 12/2006 | Sieracki et al. |
| 7,181,286 | B2 | 2/2007 | Sieracki et al. |
| 7,216,000 | B2 | 5/2007 | Sieracki et al. |
| 7,373,206 | B2 | 5/2008 | Sieracki et al. |
| 7,499,048 | B2 | 3/2009 | Sieracki et al. |
| 7,933,655 | B2 | 4/2011 | Sieracki et al. |
| 2001/0007950 | A1 | 7/2001 | North et al. |
| 2005/0010269 | A1 | 1/2005 | Lebel et al. |

OTHER PUBLICATIONS

Fowler, K. R., North, R.B.: "Patient-interactive PC interface to implanted, multichannel stimulators," Proceedings of 39th Annual Conference on Engineering in Medicine and Biology, p. 380, 1986.

North, R.B., Fowler, K.R., "Computer-controlled, patient-interactive, multichannel, implanted neurological stimulators," Applied Neurophysiology, 50:39-41, 1987.

North, R.B., Nigrin, D.I., Szymanski, R.E., Fowler, K.R., "Computer-controlled, multichannel, implanted neurological stimulation system: Clinical assessment," Pain (Suppl.), 5:S83, 1990.

Fowler, K.R., North, R.B., "Computer-optimized neurological stimulation," Proc. Ann. Internat. Conf. IEEE Engineering Medicine and Biology Soc., 13:1692-1693, 1991.

Fowler, K.R., North, R.B., "Computer-optimized neurostimulation," APL Technical Digest, 12:192-197, 1991.

North, R.B., et al., "Spinal cord stimulation for chronic intractable pain: superiority of 'multi-channel' devices," Pain, V44, pp. 119-130, 1991.

North, R.B., Fowler, K.R, "Computer-controlled, patient-interactive neurological stimulation system," (Abstract) Acta Neurochir, 117:90, 1992.

North, R.B., Fowler, K.R, Nigrin, D.A., Szymanski, R.E., "Patient interactive, computer-controlled neurological stimulation system: Clinical efficacy in spinal cord stimulator adjustment," Journal of Neurosurgery, 76:967-972, 1992.

North, R.B., Fowler, K.R, Nigrin, D.A., Szymanski, RE., Piantadosi, S., "Automated 'pain drawing' analysis by computer-controlled, patient-interactive neurological stimulation system," Pain, 50:51-57, 1992.

North, R.B., "Spinal Cord Stimulation for Chronic Intractable Pain," Electrical and Magnetic Stimulation of the Brain and Spinal Cord, pp. 289-301, 1993.

North, R.B., "The Role of Spinal Cord Stimulation in Contemporary Pain Management," APS Journal, vol. 2, No. 2, pp. 91-99, 1993.

North, R. B., Kidd, D. H., Zahurak, M., James, C. S., Long, D. M., "Spinal cord stimulation for chronic, intractable pain: Experience over two decades," Neurosurgery, 32:384-395, 1993.

North, R.B., Fowler, K.R, "Patient-interactive, microprocessor-controlled neurological stimulation system" (abstract), Stereotactic and Functional Neurosurgery, 62:309-315, 1994.

North, R. B., Levy, R. M., "Consensus conference on the neurosurgical management of pain," Neurosurgery, 34:756-761,1994.

North, R.B., McNamee, P., Wu, L., Piantadosi,S., "Artificial neural networks: Application to electrical stimulation ofthe human nervous system," (abstract) Stereotactic and Functional Neurosurgery, 65:161, 1995.

North, R. B., Kidd, D. H., Lee, M. S., Piantadosi, S., "A prospective, randomized study of spinal cord stimulation versus reoperation for the failed back surgery syndrom," Stereotactic and Functional Neurosurgery, 62:267-272, 1994.

North, R.B., et al., "Spinal Cord Stimulation for Chronic Pain," Functional Neurosurgery, vol. 6, No. 1, pp. 145-155, Jan. 1995.

North, R.B., Cutchis, P., "Spinal cord stimulation for chronic intractable pain," Spinal Cord Stimulation II, pp. 49-63, Darmstadt, Steinkopff, 1995.

North, R. B., Kidd, D. H., Wimberly, R. L., Edwin, D., "Prognostic value of psychological testing in spinal cord stimulation patients: A prospective study," Neurosurgery, 39:301-311, 1996.

North, R. B., Kidd, D. H., Zahurak, M., Piantadosi, S., "Specificity of diagnostic nerve blocks: A prospective, randomized study of sciatica due to lumbosacral spine disease," Pain, 65:77-85, 1996.

North, R.B., McNamee, P., Wu,L., Piantadosi, S., "Artificial neural networks: Application to electrical stimulation ofthe human nervous system," Neurosurgical Focus, 2(1:1):1-5, 1997.

Alo, K. M. et al., "Computer Assisted and Patient Interactive Programming of Dual Octrode Spinal Cord Stimulation in the Treatment ofChronic Pain," Neuromodulation, vol. 1, No. 1, pp. 30-45, 1998.

North, R.B., Sieracki, J.N., Fowler, K.R., Alvarez, B., Cutchis, P.N., "Patient-interactive, microprocessor-controlled neurological stimulation system," Neuromodulation, 1(4):185-193, 1998.

Khalessi, A. A., Taylor, R. S., Brigham, D. D., North, R. B., "Automated, patient interactive spinal cord stimulator adjustment: A cost-minimization analysis," Neurosurgery, 53:501-502, 2003.

North, R. B., Calkins, S. K., Campbell, D. S., Sieracki, J. M., Piantadosi, S. A., Daly, M. J., Dey, P. B., Barolat, G., "Automated, patient-interactive spinal cord stimulator" adjustment: A randomized, controlled trial, Neurosurgery 52:572-580, 2003.

Office Action dated Apr. 27, 2012 for U.S. Appl. No. 13/015,230, (7 pgs.).

Office Action dated Dec. 19, 2011 for U.S. Appl. No. 13/015,230, (7 pgs.).

Responsive Amendment dated Mar. 19, 2012 U.S. Appl. No. 13/015,230, (8 pgs.).

Office Action from U.S. Appl. No. 13/015,230, dated Sep. 12, 2012, 9 pp.

Response dated Jun. 27, 2012 for U.S. Appl. No. 13/015,230, (6 pgs.).

Office Action for U.S. Appl. No. 13/015,230, dated Jan. 17, 2013, 7 pp.

Response to Office Action dated Jan. 17, 2013, from U.S. Appl. No. 13/015,230, filed Mar. 18, 2013, 7 pages.

NEUROSTIMULATION THERAPY MANIPULATION

This application is a continuation of U.S. application Ser. No. 11/735,140, filed Apr. 13, 2007, which was a continuation of U.S. application Ser. No. 10/696,781, filed Oct. 29, 2003, which claimed the benefit of U.S. Provisional Application Ser. No. 60/422,260, filed Oct. 31, 2002, and U.S. Provisional Application Ser. No. 60/503,214, filed Sep. 15, 2003. The entire content of each of these applications is incorporated herein by reference.

TECHNICAL FIELD

The invention relates to neurostimulation therapy and, more particularly, to manipulation of neurostimulation parameters.

BACKGROUND

An implantable medical device may be used to generate electrical stimulation, and deliver the stimulation to the nervous system of a patient, i.e., to deliver neurostimulation therapy to the patient. Implantable medical devices are used to deliver neurostimulation therapy to patients to treat a variety of symptoms or conditions such as chronic pain, tremor, Parkinson's disease, epilepsy, incontinence, or gastroparesis. Typically, implantable medical devices deliver neurostimulation therapy in the form of electrical pulses via leads that include electrodes. To treat the above-identified symptoms or conditions, for example, the electrodes may be located proximate to the spinal cord, pelvic nerves, or stomach, or within the brain of a patient.

A clinician may select values for a number of programmable parameters in order to define the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient. The clinician may also select as parameters particular electrodes within an electrode set to be used to deliver the pulses, e.g., a combination of electrodes from the electrode set.

One existing programming technique used for programming spinal cord stimulation (SCS) therapy involves fixing pulse rate and width, testing a long list of electrode combinations, and asking the patient to optimize the amplitude for each. One or more electrode combinations are selected from the list, and the other parameters, e.g., pulse width and rate, are manipulated for each electrode combination to arrive at final parameter values for one or more programs. While this programming technique may involve manipulation by the patient under computer control, most neurostimulation therapy programming involves a clinician's laborious direct manipulation of parameter values.

Neurostimulation has been increasingly successful in clinical practice due to technical improvements, such as the development of leads with multiple electrode contacts, and implantable medical devices that support delivery of neurostimulation via the resulting larger electrode sets. However, complex systems with large electrode sets require increasing amounts of clinician and patient time to determine the most effective electrode combinations and stimulation parameters, i.e., program the implantable medical device to deliver neurostimulation therapy, for each patient. Further, specialized technical training may be required to effectively program such implantable medical devices, which may place even more time demands on the clinician. In other words, the potential advantages of these devices are compromised by the demands they place on valuable clinician and patient time.

SUMMARY

In general, the invention is directed toward manipulation of neurostimulation therapy parameter values. An electrical stimulation device delivers neurostimulation therapy to a patient based on values of electrical stimulation parameters. Where spinal cord stimulation (SCS) therapy is delivered, for example, the stimulation parameters may determine a location and strength of paresthesia experienced by the patient.

A user manipulates a stimulation parameter by manipulating a control device that generates a directional output based on the manipulation. A mapping system applies a calibrated map to select a value of the stimulation parameter based on the directional output of the control device. In some embodiments, the parameter values are electrode combinations, and the mapping system provides intuitive selection of electrode combinations. In particular, the mapping system may select electrode combinations such that a direction of manipulation of a directional controller of the control device corresponds to a direction of movement of paresthesia experienced by the patient. The mapping system may be calibrated based on patient paresthesia information received from a user.

In one embodiment, the invention is directed to a method comprising calibrating a map that maps an output of a control device to values of at least one electrical stimulation parameter of a stimulation device, receiving an output from the control device that reflects manipulation of a directional controller of the control device by a user, selecting a value for the electrical stimulation parameter based on the received output and the calibrated map, and providing the selected value to the stimulation device for application of electrical stimulation to a patient according to the selected value.

In another embodiment, the invention is directed to a system comprising an input circuit to receive an output from a control device, the output reflecting manipulation of a directional controller of the control device by a user, a memory to store a map that maps the output of the control device to values of at least one electrical stimulation parameter of a stimulation device, and a telemetry circuit. The system further comprises a processor to calibrate the map, select a value of the parameter based on the output of the control device and the calibrated map, and provide the selected value to a stimulation device via the telemetry circuit for application of electrical stimulation to a patient according to the selected value.

In a further embodiment, the invention is directed to a computer-readable medium containing instructions. The instructions cause a programmable processor to calibrate a map that maps an output of a control device to values of at least one electrical stimulation parameter of a stimulation device, receive an output from the control device that reflects manipulation of a directional controller of the control device by a user, select a value for the electrical stimulation parameter based on received output and the calibrated map, and provide the selected value to the stimulation device for application of electrical stimulation to a patient according to the selected value.

The invention may provide a number of advantages. For example, where the stimulation parameter manipulated is the combination of electrodes used to deliver the stimulation, the intuitive control device allows a user, such as a patient or clinician, to understand the relationship between a direction of manipulation and a direction of paresthesia movement. By providing intuitive control over a stimulation parameter, a mapping system according to the invention may allow the patient to control the stimulation parameter selection process without the assistance of a clinician. Further, the directional output of the control device provides a guided search, which allows the user, either the patient or the clinician, to select the stimulation parameter faster than a conventional trial-and-error search of all possible parameter configurations.

Additionally, the map is calibrated for each patient based on individual paresthesia information. Calibrating the map allows the control device to be mapped precisely to unique electrode positions and orientations, and unique anatomies and physiologies presented by different patients. The calibration technique also allows an amplitude scale factor to be built into the directional output of the control device. Therefore, when the user manipulates the control device to move the region of paresthesia, the amplitude will automatically scale to avoid an unexpected increase in amplitude of the electrical stimulation.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
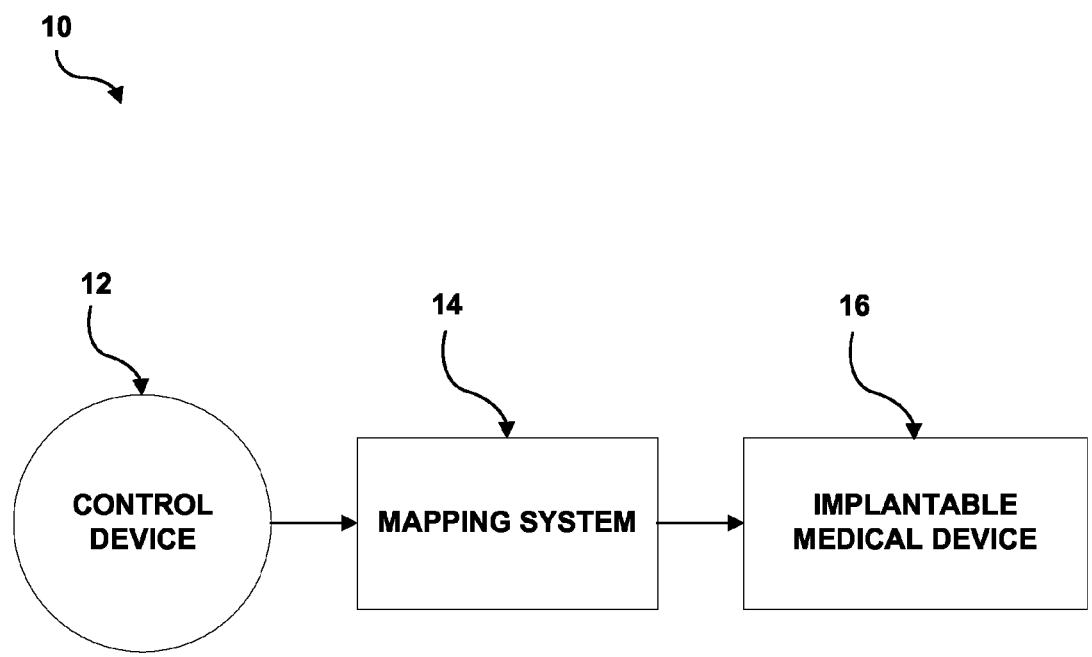
FIG. 1 is a block diagram illustrating an example electrical stimulation system that includes a control device and a mapping system according to the invention.

FIG. 1 is a block diagram illustrating an electrical stimulation system 10. Electrical stimulation system 10 includes a control device 12, a mapping system 14, and an electrical stimulation device, which in this case takes the form of an implantable medical device (IMD) 16. IMD 16 is used to deliver neurostimulation therapy to a patient (not shown in FIG. 1). IMD 16 may deliver neurostimulation in the form of electrical pulses to treat a symptom or condition of the patient, such as chronic pain, tremor, Parkinson's disease, epilepsy, incontinence, or gastroparesis.

Mapping system 14 and control device 12 may operate with, or be part of, a programming device or system used by a clinician (not shown), and in some cases the patient, to program delivery of neurostimulation by IMD 16. In some embodiments, control device 12 and mapping system 14 are embodied in separate physical devices, and communicate via any of a variety of known wired or wireless connections. In some embodiments, mapping system is embodied within a computing device, and may be embodied as software executed by a processor of the computing device. The computing device may be the programming device used by the clinician, and in some cases the patient, to program IMD 16. In some embodiments, a single device, such as the programming device, includes both control device 12 and mapping system 14.

Control device 12 allows a user to manipulate one or more electrical stimulation parameters of IMD 16. Exemplary electrical stimulation parameters include electrode combination, pulse rate, pulse width and current or voltage pulse amplitude. As will be described in greater detail below, control device 12 includes a directional controller such as a knob, a wheel, a joystick, a mouse, arrow keys on a keyboard, or the like, and generates a directional output that indicates a direction of manipulation of the directional controller by a user, such as the clinician or the patient.

Mapping system 14 uses a calibrated map to map the directional output of control device 12 to values of one or more of the stimulation parameters of IMD 16. Mapping system 14 selects values of the stimulation parameter based on the directional output, and provides the selected values to IMD 16. IMD 16 generates and delivers electrical stimulation according to the selected parameter values.

In exemplary embodiments, such as where IMD 16 is used to deliver spinal cord stimulation (SCS) therapy, the values of the stimulation parameter are combinations of electrodes, and a direction of movement of a paresthesia region is based on the direction of manipulation of the directional controller of control device 12 by the user. For example, as the user manipulates the directional controller in an upward direction, the paresthesia experienced by the patient moves up the patient's body. Mapping system 14 may take input from control device 12 either directionally, allowing the user to manipulate step-by-step or smoothly in an indicated direction, or spatially, allowing the user to indicate by location where in the overall range of adjustment the stimulation is desired.

Mapping system 14 and control device 12 may be used to program a plurality of IMDs 16 for a plurality of patients, and mapping system 14 may calibrate a map for each patient to correctly map the directional output of control device 12 to the arrangement of electrodes implanted within the patient. As will be described in greater detail below, mapping system 14 may initially select a fixed map based on information that describes the configuration of an electrode set implanted within the a patient, which may be input to mapping system 14 by the user. Mapping system 14 may then adapt the fixed map based on paresthesia information input to mapping system 14 by the user. Mapping system 14 may be calibrated either before or during use of electrical stimulation system 10, or both.

Before use, mapping system 14 may be calibrated by the user manipulating control device 12 to several predetermined locations on the fixed map, i.e., predetermined locations within a manipulation range of the directional controller, and inputting paresthesia information at each location. The predetermined locations may comprise two corners of the fixed map, or four corners and a center point. The resulting map may be a liner or non-linear adaptation. The user may enter the paresthesia information by indicating regions of paresthesia on a body template. During use, mapping system 14 may continually calibrate a map by factoring received paresthesia and location information into the map. However, the invention is not limited to embodiments where map is calibrated during programming, or even to embodiments where paresthesia information is received from a user during programming. Mapping system 14 may apply Euclidian transforms for linear adaptation of a fixed map, or non-Euclidian transforms to accommodate for non-linearity and twists in the configuration of the electrode set implanted within the patient.

At each calibration location the user may input a minimum perception amplitude level of the stimulation pulse as paresthesia information, which may be used by mapping system 14 to adapt a fixed map as described above. The identified amplitude level may also allow mapping system 14 to create an amplitude scale factor to apply to electrode combinations within the map. In embodiments where the map includes amplitude scale factors for electrode combinations, the patient may then avoid an unexpected increase in amplitude of the electrical pulse generated by IMD 16 during paresthesia manipulation. The user may further adjust the amplitude to a comfortable level at any manipulation location.

Control device 12 and mapping system 14 may increase user efficiency when searching for stimulation parameters that produce effective paresthesia, e.g., programming IMD 16, which may reduce the amount of clinician and patient time required for a programming session. In particular, mapping system 14 may provide an intuitive relationship between manipulation of a directional controller of control device 12 and values of a stimulation parameter. In exemplary embodiments where IMD 16 delivers SCS therapy, the user manipulates the directional controller in a direction, and mapping system selects an electrode combination such that a region of paresthesia experienced by the patient also moves in the direction. Consequently, the user may be able to intuitively move the region of paresthesia to the location of the patient's pain, and, therefore, more quickly select an appropriate electrode combination for inclusion in a program.

The invention is not, however, limited to use of control device 12 and mapping system 14 during a programming session. In some embodiments, control device 12 and mapping system 14 may be included in a programming device used by the patient for long-term adjustment and control of delivered neurostimulation, e.g., a patient programming device. In such embodiments, the patient may manipulate control device 12 to alter the electrical stimulation provided during different times of the day or when the patient is in different positions.

Figure 2:
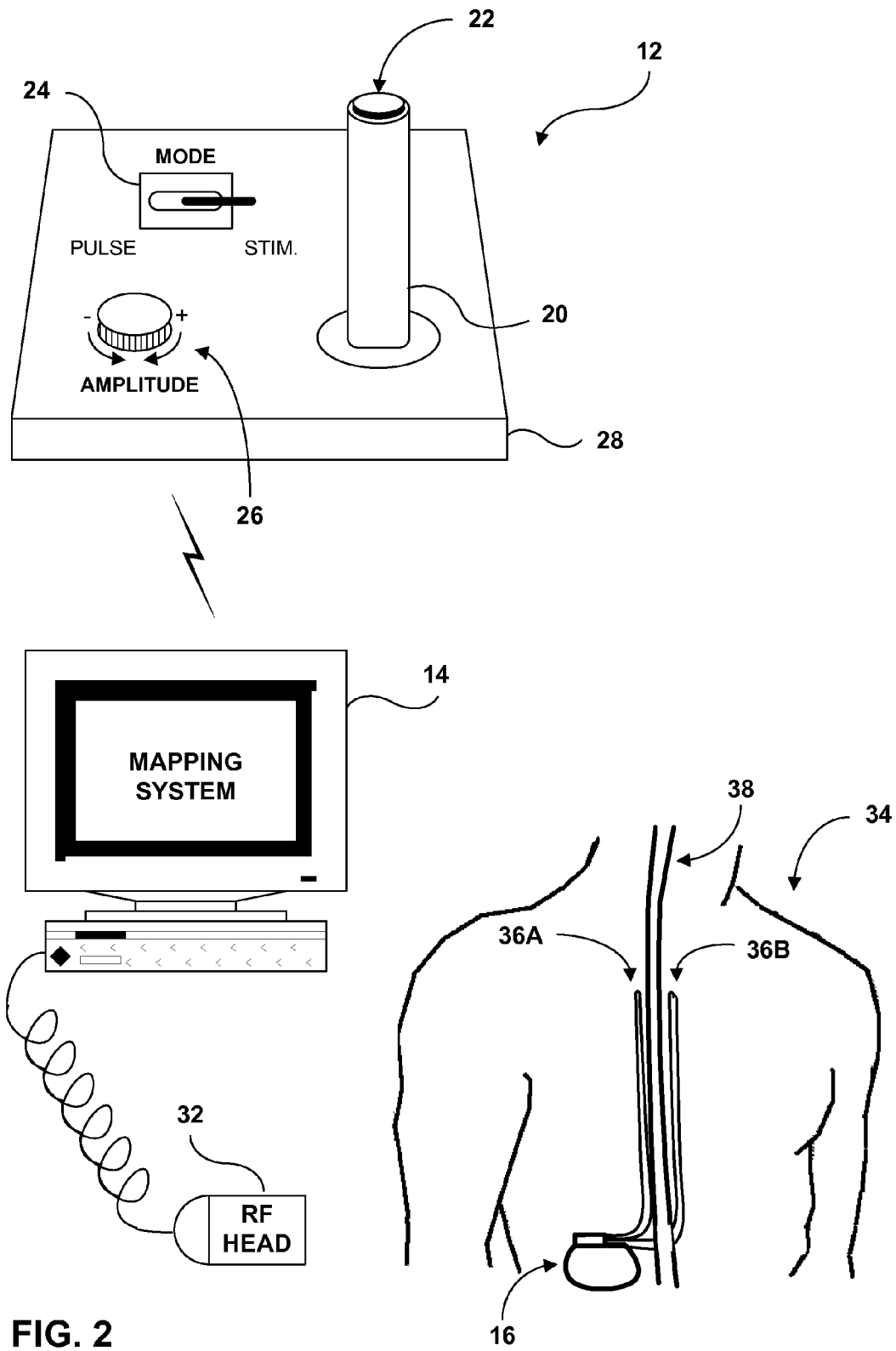
FIG. 2 is a schematic diagram illustrating the example electrical stimulation system of FIG. 1 in greater detail.

FIG. 2 is a schematic diagram illustrating the example electrical stimulation system of FIG. 1 in greater detail. Electrical stimulation system 10 operates as described in reference to FIG. 1, and again includes a control device 12, a mapping system 14, and an IMD 16. In the illustrated embodiment IMD 16 is coupled to leads 36A and 36B (collectively "leads 36") that extend to positions proximate to a spinal cord 38 of a patient 34. Leads 36 include electrodes (not shown in FIG. 2), and IMD 16 may deliver SCS therapy in the form of electrical stimulation pulses via the electrodes.

As shown in FIG. 2, a directional controller 20, a mode operation switch 24, and an amplitude adjustment knob 26 are disposed within and/or on a housing 28 of control device 12. In the illustrated embodiment, directional controller 20 is a joystick, and indicator button 22 is disposed on directional controller 20. In other embodiments, any or all of directional controller 20, indicator button 22, mode operation switch 24, and amplitude adjustment knob 26 may be software screen objects on a display. For example, in some embodiments, directional controller 20 may take the form of a representation of a joystick on a touch-screen display that is capable of being manipulated by a user. Further, operation mode switch 26 may be a rocker, a lever, a button, a key on a keyboard, a mouse, or the like.

Control device 12 generates an output as a function of the direction of manipulation of directional controller 20. As described above, mapping system 14 uses a calibrated map to select a value for a stimulation parameter based on the output of control device 12. In some embodiments, mapping device 14 is capable of using multiple calibrated maps, each map corresponding to a different stimulation parameter. In such embodiments, mapping system 14 may select one of the maps based on an operation mode designated by operation mode switch 24, e.g., the position of switch 24.

Where, as shown in FIG. 2, switch 24 is disposed on control device 12, control device 12 sends a signal to mapping system 14 indicating the mode. Mapping system 14 selects one of the maps based on the signal. In other embodiments, operational mode switch 24 may be located on, and a component of, mapping system 14.

In the illustrated embodiment, the operation modes available for selection by a user via switch 24 include a stimulation mode and a pulse mode. When the user selects stimulation mode, mapping system 14 selects a calibrated map that maps the output of control device 12 to combinations of the electrodes located on leads 36. In other words, when mapping system 14 is operating in the stimulation mode, a user may use directional controller 20 to select electrode combinations. When the user selects pulse mode, mapping system selects a map that maps the output of control device 12 to one or more of stimulation pulse amplitude, width and rate, and the user may use directional controller 20 to adjust pulse amplitude, width and/or rate.

An exemplary technique that may be employed by a user, e.g., the clinician and/or patient 34, to select stimulation parameters for inclusion in one or more programs using control device 12 and mapping system 14 involves use of mode switch 24. The user selects stimulation mode using switch 24, holding the width and rate of the pulses generated by IMD 16 constant while manipulating directional controller 20 to search for an electrode combination that provides effective stimulation to patient 34. When an effective electrode combination is identified, the user may switch operation mode switch 24 to the pulse mode and manipulate the amplitude, width and/or rate of the generated stimulation pulse to see if the effectiveness of a program including the identified electrode combination can be improved.

In the case of the stimulation mode, the direction of manipulation of directional controller 20 corresponds to the direction of movement of a paresthesia region within patient 34. In the case of the pulse mode, the direction of vertical manipulation of directional controller 20 corresponds to either increasing or decreasing the pulse amplitude, width and/or rate. The user may also manipulate pulse amplitude using amplitude adjustment knob 26.

The effective electrode combination may be stored by mapping system 14 to be recalled later for application to IMD 16, e.g., for further refinement of a program including the electrode combination. A user may cause mapping system 14 to store a plurality of parameters by pressing indicator button 22 when directional controller 20 is in a position that provides adequate paresthesia In the embodiment illustrated in FIG. 2, control device 12 communicates wirelessly with mapping system 14. Control device 12 and mapping system 14 may, for example, communicate via a radio frequency or infrared media, as is known in the art. Mapping system 14, in this case, takes the form of a computing device that is coupled to an RF programming head 32. Mapping system uses RF programming head 32 to transmit the electrical stimulation parameter values selected based on the output of control device 12 to IMD 16 via device telemetry as is known in the art. IMD 16 receives the stimulation parameters and generates a stimulation pulse based on the values.

Figure 3:
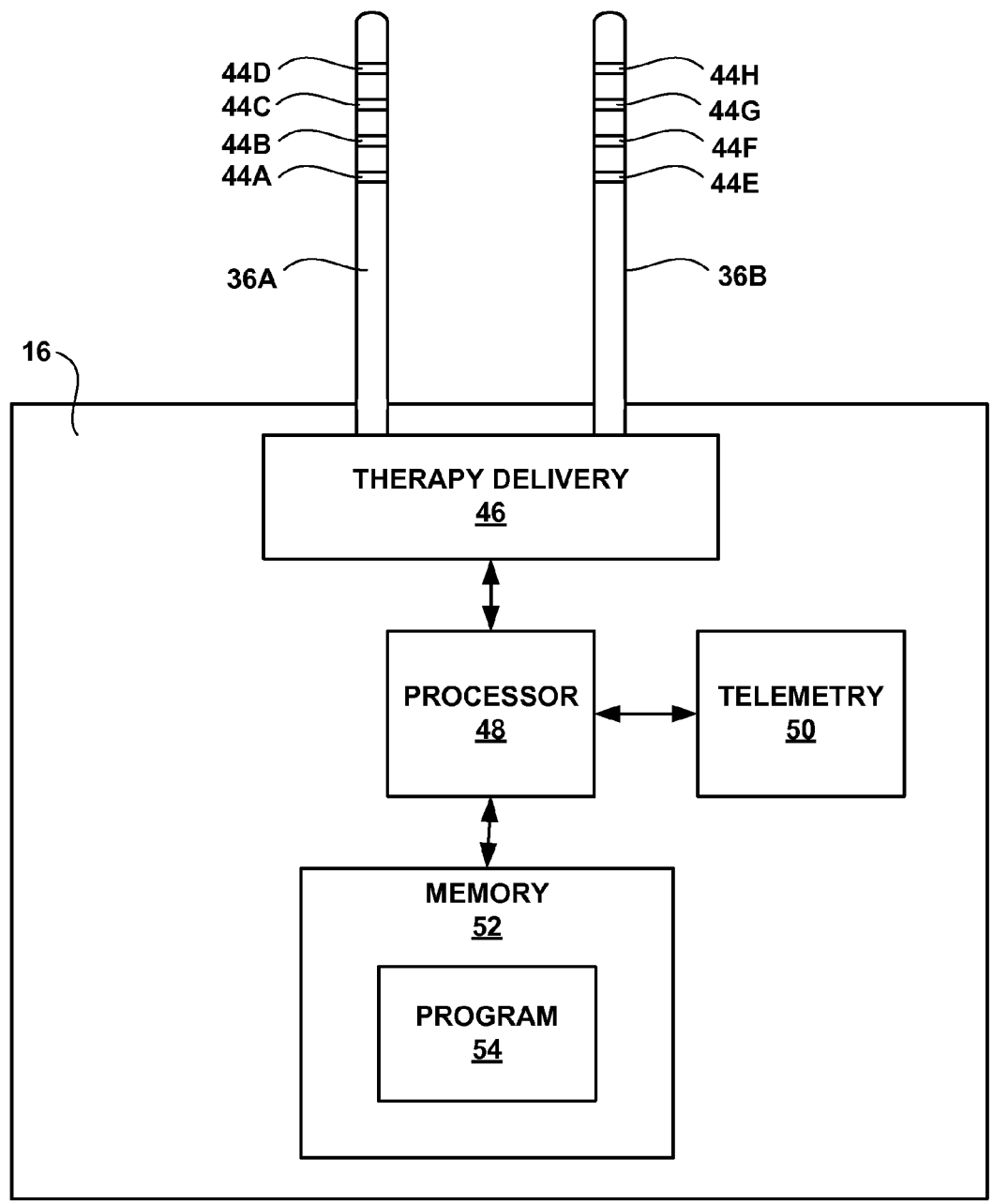
FIG. 3 is a block diagram illustrating an example configuration of an implantable medical device of the electrical stimulation system of FIGS. 1 and 2.

FIG. 3 is a block diagram illustrating an example configuration of IMD 16. IMD 16 may deliver neurostimulation therapy via electrodes 44A-D of lead 36A and electrodes 44E-H of lead 36B (collectively "electrodes 44"). Electrodes 44 may be ring electrodes. The configuration, type, and number of electrodes 44 illustrated in FIG. 3 are merely exemplary.

IMD 16 includes a therapy delivery circuit 46, a processor 48, a telemetry circuit 50, a memory 52, and a program 54 stored in memory 52. Electrodes 44 are electrically coupled to therapy delivery circuit 46 via leads 36. Therapy delivery circuit 46 may, for example, include an output pulse generator coupled to a power source such as a battery. Therapy delivery circuit 46 may deliver electrical pulses to patient 34 via at least some of electrodes 44 under the control of a processor 48.

Processor 48 controls therapy delivery circuit 46 to deliver stimulation according to program 54. Specifically, processor 48 may control circuit 46 to deliver electrical stimulation pulses with an amplitude, width, and rate specified by program 54. Processor 48 may also control circuit 46 to deliver the pulses via a selected subset of electrodes 44 with selected polarities, as specified by program 54. Processor 48 may include a microprocessor, a controller, a digital signal processor (DSP), an application specific integrated circuit (ASIC), a field-programmable gate array (FPGA), discrete logic circuitry, or the like.

Telemetry circuit 50 allows processor 48 to communicate with mapping system 14. During the programming process described above, processor 48 receives values of one or more stimulation parameters selected by mapping system 14 based on the output of control device 12 via telemetry circuit 50, and stores with values within memory 52 as part of program 54. Processor 48 may update program 54, and direct therapy delivery circuit 46 to deliver stimulation pulse according to new values for a stimulation parameter as new values for a parameter are received from mapping system.

In addition to program 54, memory 52 may include program instructions that, when executed by processor 48, cause IMD 16 to perform the functions ascribed to IMD 16 herein. Memory 52 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like.

Figure 4:
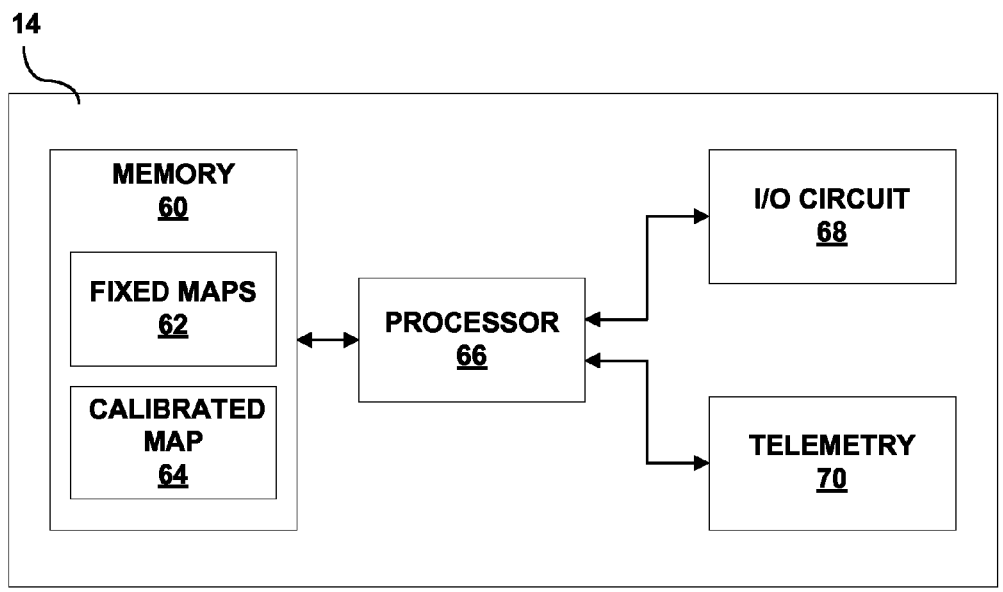
FIG. 4 is a block diagram illustrating an example configuration of the mapping system of the electrical stimulation system of FIGS. 1 and 2.

FIG. 4 is a block diagram illustrating an example configuration of mapping system 14. Mapping system 14 includes a memory 60 that stores fixed maps 62 and a calibrated map 64, a processor 66, an input/output (I/O) circuit 68, and a telemetry circuit 70. As described above, mapping system 14 may operate with, be part of, or may be a programming device or system used by a clinician (not shown), and in some cases patient 34, to program delivery of neurostimulation by IMD 16.

Processor 66 receives an output form control device 12 via I/O circuit 68. Processor 66 uses calibrated map 64 to select values of a stimulation parameter based on the output of control device 12, and transmits selected parameter values to IMD 16 via telemetry circuit 70 for application of neurostimulation according to the parameter value to patient 34. Mapping system 14 may include RF programming head 32 (FIG. 2) coupled to telemetry circuit 70 to transmit the stimulation parameter to IMD 16.

In exemplary embodiments, processor 66 receives electrode arrangement, type, and number information from a user via I/O circuit 68. Additional information received via I/O circuit 68 may include pulse width and rate values, amplitude levels, and pain and paresthesia region indications made by a user on a body diagram. The dynamic body diagram may comprise an outline template of a body displayed on a display (not shown) coupled to mapping system 14. The region indications may be made by the user with a mouse, or the display may be a touch screen and the user may use a stylus to indicate regions on the body diagram. In some embodiments, the display and/or a pointing device may be part of control device 12, which provides the information to processor 66 via I/O circuit 68.

Processor 66 determines which of fixed maps 62 stored in memory 60 best matches the received electrode information, and calibrates the selected fixed map 62 to generate calibrated map 64. The selected fixed map 62 may be calibrated by the user manipulating directional controller to locations within the selected fixed map 62, e.g., locations within the manipulation range of directional controller 20, and entering paresthesia information including the body diagram indications and a minimum amplitude level at which paresthesia is perceived by patient 34. Processor 66 uses the received location and paresthesia information to adapt the selected fixed map 62, i.e., generate calibrated map 64 for patient 34.

By generating calibrated maps 64, mapping system 14 may account for patient-to-patient differences in electrode position and orientation, and nervous system anatomy and physiology. In particular, where IMD 16 is used to deliver SCS therapy and calibrated map 64 maps a directional output of control device 12 to electrode combinations, generation of calibrated map 64 by mapping system 14 may enable a direction of manipulation of directional controller 20 to correspond to a direction of movement of paresthesia experienced by patient 34. In some embodiments, map 64 may be further calibrated by paresthesia information received while mapping system 14 is being used by a user, such as a clinician or patient, to test stimulation parameters for inclusion in a program.

Processor 66 may include a microprocessor, a controller, a DSP, an ASIC, an FPGA, discrete logic circuitry, or the like. In addition to maps 62, 64, memory 60 may store program instructions that, when executed by processor 66, cause mapping system 14 to perform the functions ascribed to mapping system 14 herein. Memory 60 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 5:
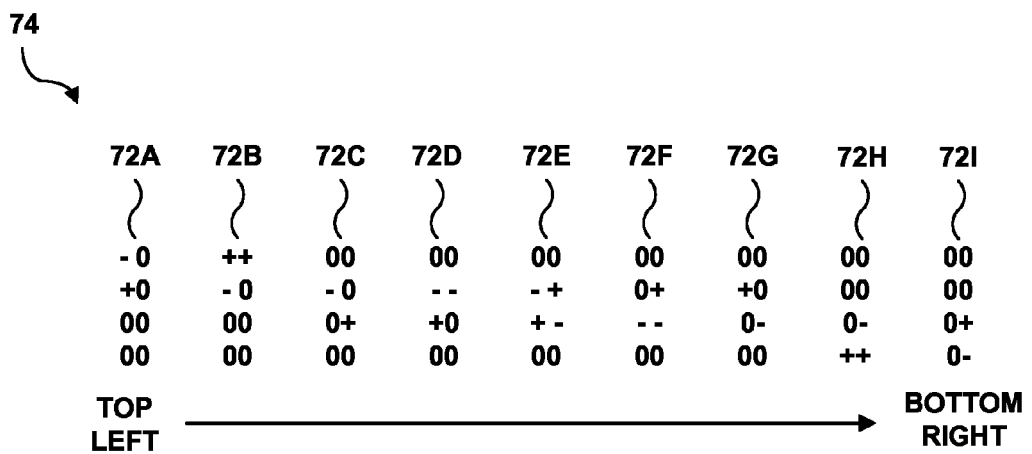
FIG. 5 is a diagram illustrating an exemplary fixed map that may be calibrated and used by the mapping system of FIGS. 1, 2 and 4 to map an output of the control device to a value of an electrical stimulation parameter.

FIG. 5 is a diagram illustrating an exemplary fixed map 74 that may be calibrated and used by mapping system 14 to map an output of control device 12 to one of electrode combinations 72A-I (hereinafter "electrode combinations 72"). Fixed map 74 may be one of fixed maps 62 available for selection by mapping system 14. Fixed map 74 corresponds to an eight contact electrode set, with four contacts on each of two leads. Consequently, mapping system 14 may select fixed map 74 if information describing the configuration of electrodes 44 within patient 34 matches this description. Such a configuration is typically used for delivery of SCS therapy, with the electrodes may be placed essentially parallel to spinal cord 38 with four electrodes left and four electrodes right of the midline.

Electrode combinations 72 identify the polarity of each of the electrodes of an electrode set according to that combination. Electrode contacts that are off are represented with a "0", and those that are on are represented with a "+" for an anode and a "−" for a cathode. The illustrated combinations 72 are combinations that would be selected by mapping device 14 during movement of directional controller 20 from a top left position to a bottom right position within its manipulation range.

Fixed map 74 may include other combinations 72 (not shown) that correspond to movement to other locations and in other directions within the manipulation range of directional controller 20. Further, when calibrated by mapping system 14, the combinations 72 associated with various positions within the manipulation range of directional controller 20 may be altered from those of fixed map 74 to create calibrated map 64. Specifically, combinations 72 may be altered to account for patient-to-patient electrode configuration, anatomical and physiological differences, such that the position to which directional controller 20 is manipulated within its manipulation range corresponds to the direction of movement of paresthesia within patient 34.

Figure 6:
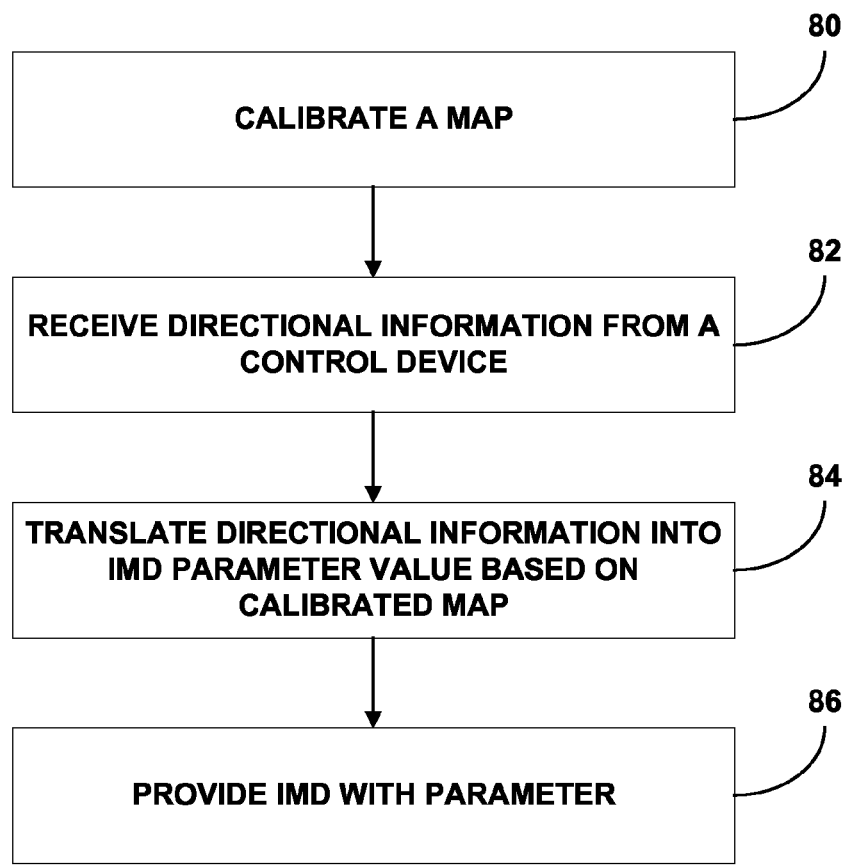
FIG. 6 is a flow chart illustrating an example method that may be employed by a mapping system to map an output of a control device to a value of an electrical stimulation parameter.

FIG. 6 is a flow chart illustrating an example method that may be employed by mapping system 14 to map an output of a control device to a value of an electrical stimulation parameter. Mapping system 14 receives electrode arrangement, type, and number information from a user regarding the set of electrodes 44 implanted within patient 34. Processor 66 of mapping system 14 selects one of fixed maps 62 stored in memory 60 that closely matches the received electrode information. The selected fixed map is calibrated (80) based on location and paresthesia information received by mapping system 14 via I/O device 68. In some embodiments, the location and paresthesia information is received via control device 12. The calibration may include altering electrode combinations of the selected fixed map 62 to match the direction of movement of paresthesia for patient 34 to the direction of movement of a directional controller 20 of control device 12. Processor 66 stores the calibrated map 64 in memory 60.

Mapping system 14 receives directional output from user manipulation of control device 12 (82). In exemplary embodiments, the directional output reflects a direction of manipulation of a directional controller of control device 12. Mapping system 14 applies calibrated map 64 to map the received directional output to a value of an electrical stimulation parameter of IMD 16 (84). Once the corresponding electrical stimulation parameter value is selected, processor 66 transmits the parameter value to IMD 16 (86) via telemetry circuit 70. IMD 16 may then generate electrical stimulation pulses according to the received parameter value for delivery to patient 34.

Figure 7:
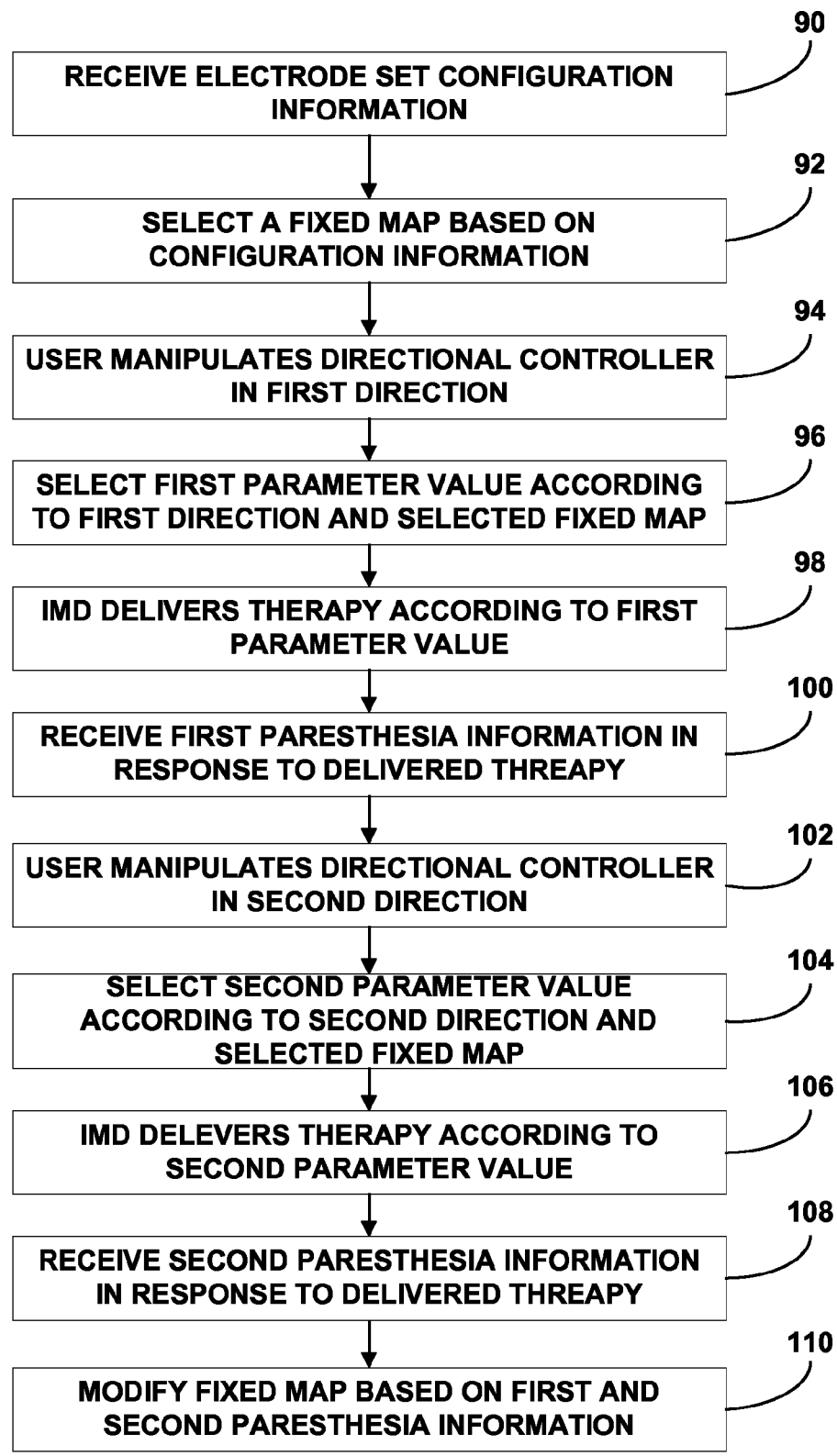
FIG. 7 is a flow chart illustrating an example fixed map calibration method that may be employed by a mapping system.

FIG. 7 is a flow chart illustrating an example fixed map calibration method that may be employed by mapping system 14. Mapping system 14 receives electrode arrangement, type, and number information (90) from a user describing the configuration of electrodes 44 within patient 34. Processor 66 of mapping system 14 selects one of fixed maps 62 stored in memory 60 that closely matches the received electrode information (92). Processor 66 receives a first directional output from user manipulation of directional controller 20 of control device 12 in a first direction via I/O circuit 68 (94). Processor 66 applies the selected fixed map 62 to select a first value for an electrical stimulation parameter, e.g., a first electrode combination, based on the first directional output (96). Once the corresponding first electrical stimulation parameter value is selected, processor 66 transmits the parameter value to IMD 16 via telemetry circuit 70. IMD 16 may then generate and deliver stimulation pulses according to the selected parameter value to patient 34 (98). Processor 66 receives first patient paresthesia information from the user as a response to the applied stimulation pulse (100). In some embodiments, as described above, the paresthesia information may include information indicating a region of paresthesia on a body template image, and/or a pulse amplitude value associated with paresthesia perception.

Processor 66 then receives a second directional output from user manipulation of directional controller 20 in a second direction (102). Processor 66 applies the selected fixed map 62 to select a second value for the electrical stimulation parameter, e.g., a second electrode combination 72, based on the second directional output (104). Once the corresponding second electrical stimulation parameter value is selected, processor 66 transmits the parameter value to IMD 16 via telemetry circuit 70. IMD 16 may then generate and deliver electrical stimulation pulses according to the second parameter value to patient 34 (106). Processor 66 receives second patient paresthesia information from the user as a response to the applied stimulation pulse (108).

Processor 66 modifies the selected fixed map 62 based on the first and second paresthesia information (110) received by mapping system 14 from control device 12 via I/O circuit 68. Processor 66 in mapping system 14 stores the modified fixed map as calibrated map 64 in memory 60. In exemplary embodiments, the modification may include altering electrode combinations 72 of the selected fixed map 62 such that a direction of movement of paresthesia for patient 34 corresponds to the direction of the manipulation of directional controller 20.

In some embodiments, the user manipulates directional controller 20 in a first and second direction by manipulating directional controller 20 to diametrically opposed corners of a manipulation range of directional controller 20. In some embodiments, the user manipulates directional controller 20 in additional directions during calibration. For example, the user may in some embodiments manipulate directional controller 20 to four corners and a center point of a manipulation range of directional controller 20. In such embodiments, processor 66 receives paresthesia information describing paresthesia experienced by patient 34 at each of these locations for generation of calibrated map 64 based on the paresthesia information.

Figure 8:
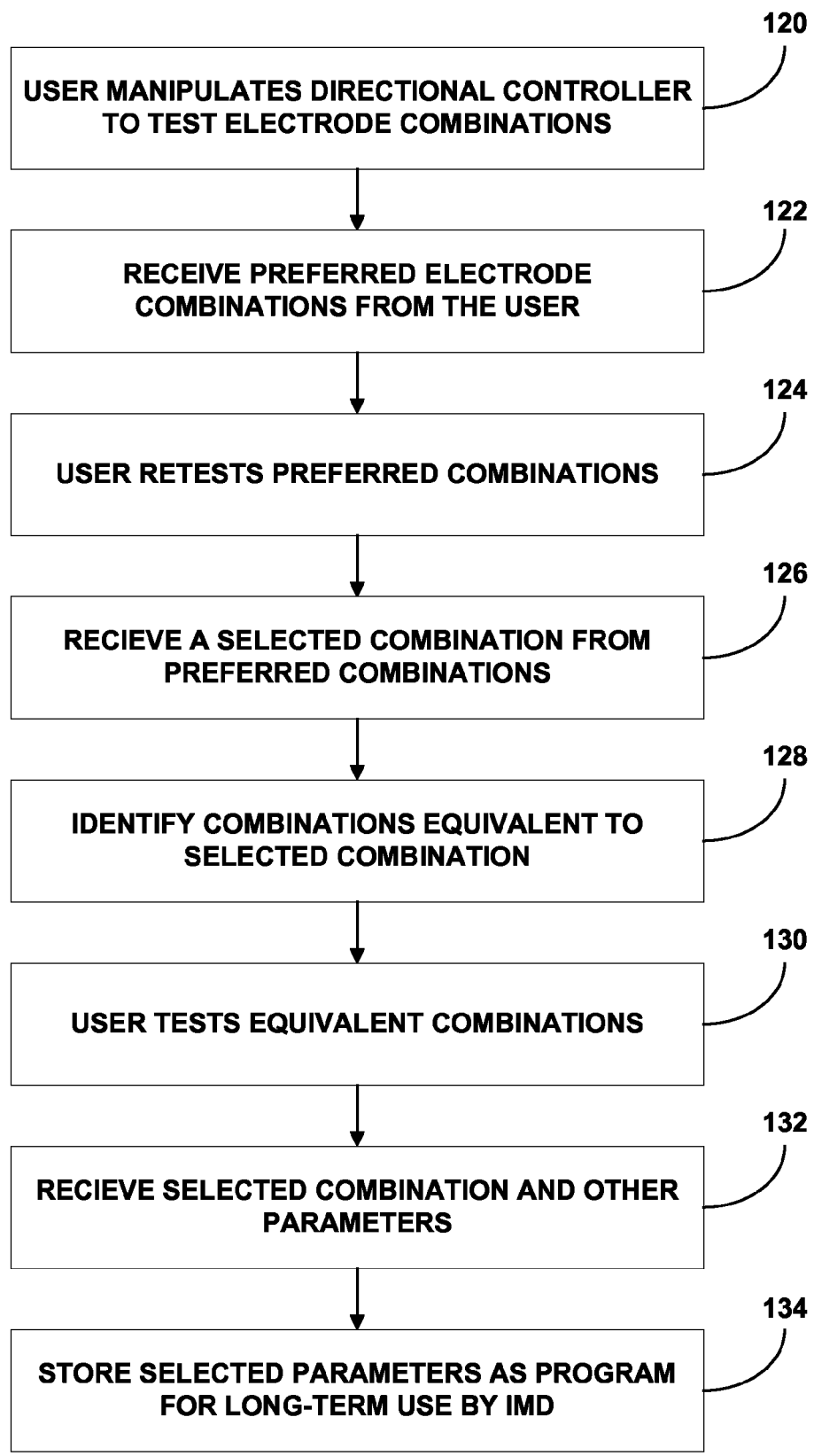
FIG. 8 is a flow chart illustrating an example electrode combination and neurostimulation program selection method that may be employed by a mapping system.

FIG. 8 is a flow chart illustrating an example electrode combination and neurostimulation program selection method that may be employed by mapping system 14. Mapping system 14 receives a directional output from control device based on user manipulation of directional controller 20. In the case of multiple operation modes, the directional output is mapped to electrode combinations when control device 12 is in the stimulation mode.

The user manipulates directional controller 20 to test regions of paresthesia generated by different electrode combinations (120). Mapping system 14 receives a user indication from control device 12 when an electrode combination creates an effective paresthesia region (122) for patient 34. For example, the user may identify effective combinations by pressing indicator button 22 when directional controller 20 is in a position that produces effective paresthesia.

The preferred combinations are stored in memory 60 of mapping system 14 for retesting by the user (124). During retesting, the user may further use control device 12 to improve the effects of the stored electrode combinations by, for example, moving mode switch 24 and using directional controller 20 to alter additional electrical stimulation parameters of a program associated with the electrode combination. For example, the user may manipulate directional controller up and down to increase and decrease stimulation parameters, such as pulse amplitude, width and rate. In some embodiments, control device 12 may include a dedicated amplitude knob 26 for adjustment of pulse amplitude.

Mapping system 14 receives an electrode combination selected by the user (126) during retesting. In some embodiments, processor 66 may further modify calibrated map 64 so that the selected combination corresponds to a center of a manipulation range of directional controller 20. With calibrated map 64 so modified, a user may more easily test electrode combinations that are "adjacent" to the store electrode combinations.

Mapping system 14 may store additional information describing possible electrode combinations that are not represented within a calibrated map 64 within memory 60. Based on the received electrode arrangement, type, and number information, processor 66 may, in some embodiments, identify electrode combinations not represented within calibrated map 64 that produce stimulation therapy substantially equivalent to the user selected combination (128). The user may test the equivalent combinations (130) by controlling mapping system 14 to provide the equivalent combination to IMD 16 to, for example, identify the combination that generates effective paresthesia while using the least amount of power or the fewest electrodes. Processor 66 receives an electrode combination selected by the user from the equivalent and or adjacent electrode combinations, along with additional parameters (132) such as an amplitude level, and pulse width and rate values, and transmits the parameters to IMD 16 via telemetry circuit 70. IMD 16 stores the parameters as a program 54 (134) in memory 52 of IMD 16 that is the result of the programming process, which will thereafter be available for use by processor 48 to control delivery of neurostimulation therapy to patient 34 outside of the clinical setting.

Figure 9:
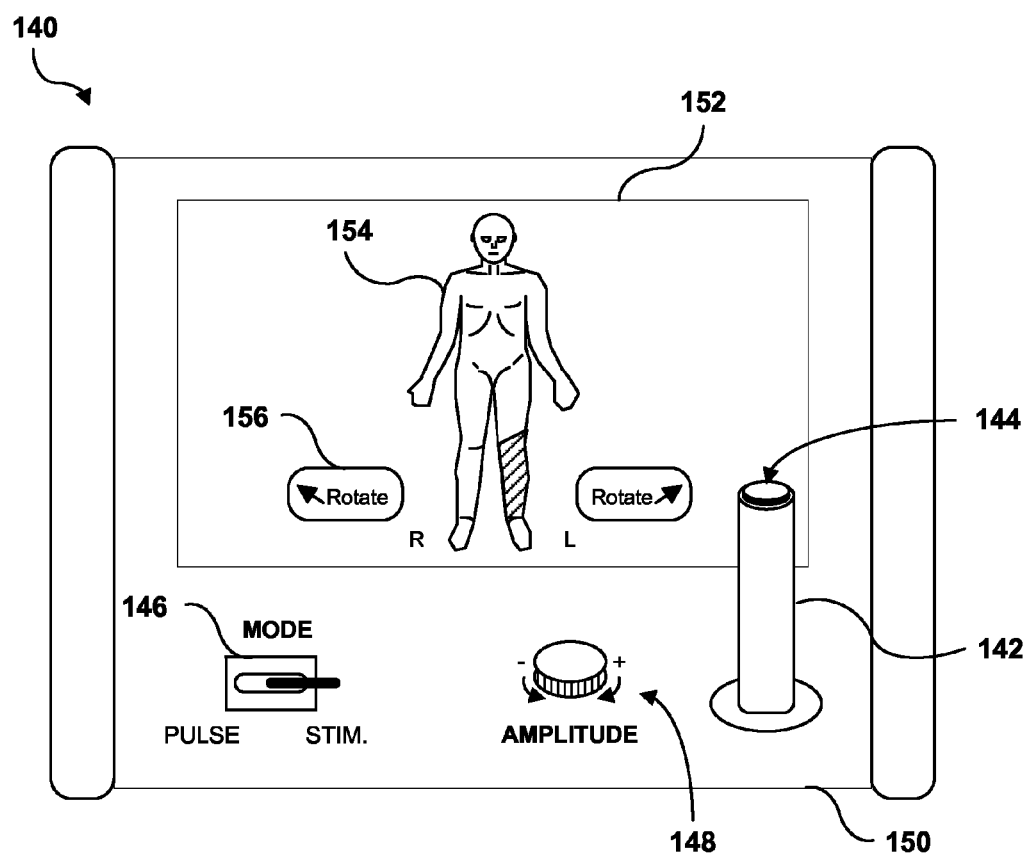
FIG. 9 is a schematic diagram illustrating another example embodiment of a control device.

FIG. 9 is a schematic diagram illustrating another example embodiment of a control device 140. As shown in FIG. 9, control device 140 includes a directional controller 142, an indicator button 144, a mode operation switch 146, an amplitude adjustment knob 148, a housing 150, which may be similar to directional controller 20, indicator button 22, mode operation switch 24, amplitude adjustment knob 26, and housing 28 of control device 12 described above with reference FIG. 2. Control device 140 additionally includes a display screen 152 with a dynamic body template 154 and body template control buttons 156 displayed on display screen 152. As described above with reference to FIG. 2, any or all of directional controller 142, indicator button 144, mode operation switch 146, and amplitude adjustment knob 148 may be software screen objects on display screen 152. For example, in some embodiments, directional controller 142 may take the form of a representation of a joystick on a touch-screen display 152 that is capable of being manipulated by a user.

In exemplary embodiments, mapping system 14 may be implemented as software executed by a processor (not shown) of control device 140. In other words, a mapping system 14 according to the invention may comprise a control device 12, 140. Further, control device 140 that implements mapping system 14 may be a clinician programming device used to program for programming IMD 16, and may provide additional functionality known in the art to be provided by such devices, such as collection of demographic or symptom information from patient 34. A control device 140 that implements mapping system 14 may be coupled to RF programming head 32 to deliver electrical stimulation parameter values to IMD 16.

A user may input pain and/or paresthesia region indications to mapping system 14 via dynamic body template 154. Display screen 152 may be a touch screen to accept the body region indications via a stylus (not shown); otherwise a pointing device, such as a mouse may be coupled to control device 140 and used by the user to indicate the body regions on display screen 152. Body template control buttons 156 allow the user to view additional dynamic body templates in order to specify pain and/or paresthesia experienced by patient 34 on his or her sides or back.

Display screen 152 may also display parameter values. For example, the selected electrode combinations may be illustrated on display screen 152 during testing. The pulse width and rate values for the applied stimulation pulse may be displayed, as well as the amplitude level. In this way, the user may relate the parameter values with the resulting paresthesia and further reduce the amount of time needed to select stimulation parameters.

Various embodiments of the invention have been described. However, one skilled in the art will appreciate that various modifications may be made to these embodiments without departing from the scope of the invention. For example, one embodiment described includes a method for adapting a fixed electrode combination map to a specific patient. The fixed map is chosen by a processor in a mapping system based on electrode configuration information received from a user. However, if the patient's electrode configuration is substantially identical to one of the fixed maps, then adapting the map may not be necessary. In that case, the fixed map may still be calibrated to generate an amplitude scale factor, but the calibration will not alter the electrode combination order of the fixed map. These and other embodiments are within the scope of the following claims.

The invention claimed is:

1. A method comprising:
    storing an electrode combination map that maps an output of a control device to a predetermined subset of electrode combinations available from a set of electrodes implanted within a patient, wherein the electrode combinations specify polarities of electrodes of the set of electrodes;
    receiving the output from the control device, wherein the output reflects manipulation of a directional controller of the control device by a user;
    selecting one electrode combination of the predetermined subset of electrode combinations based on the received output and the electrode combination map; and
    controlling a stimulation device coupled to the set of electrodes to apply electrical stimulation to the patient via the selected electrode combination.

2. The method of claim 1, wherein the output of the control device comprises directional information that reflects a direction of a manipulation of the directional controller, and selecting the electrode combination comprises selecting the electrode combination such that a direction of movement of paresthesia resulting from application of electrical stimulation via the selected electrode combination reflects the direction of the manipulation of the directional controller.

3. The method of claim 1, further comprising:
    storing a plurality of electrode combination maps, each of the electrode combination maps mapping the output of the control device to a respective predetermined subset of electrode combinations available from one of a plurality of electrode set configurations;

receiving information that describes a configuration of the set of electrodes coupled to the stimulation device; and selecting the electrode combination map based on the configuration information.

4. The method of claim 1, wherein the user manipulates the directional controller to test a plurality of electrode combinations by application of electrical stimulation from the stimulation device to the patient via the plurality of electrode combinations.

5. The method of claim 4, further comprising:

identifying one of the tested electrode combinations based on input received from the user via the control device; and recalibrating the map such that a center position of a manipulation range of the directional controller corresponds to the identified electrode combination.

6. The method of claim 4, wherein the map comprises amplitude scale factors associated with at least some of the electrode combinations, the method further comprising determining the amplitude scale factors based on paresthesia information received from the user during the testing.

7. The method of claim 4, further comprising:

identifying one of the tested electrode combinations based on input received from the user via the control device; and storing the identified electrode combination for reapplication by the stimulation device at a later time.

8. The method of claim 1, wherein the set of electrodes are implanted proximate to the spinal cord of the patient, and the electrical stimulation comprises spinal cord stimulation.

9. The method of claim 1, wherein each of the predetermined subset of electrode combinations corresponds to a respective stimulation location.

10. The method of claim 9, wherein each of the predetermined subset of electrode combinations corresponds to a respective paresthesia location.

11. The method of claim 9, wherein the set of electrodes comprises a two dimensional array of electrodes, and the mapping of the subset of electrode combinations to the output of the control device enables the user to move the stimulation longitudinally and laterally.

12. A mapping system comprising:

an input circuit configured to receive an output from a control device, the output reflecting manipulation of a directional controller of the control device by a user;

an electrode combination map that maps the output of the control device to a predetermined subset of electrode combinations available from a set of electrodes implanted within a patient, wherein the electrode combinations specify polarities of electrodes of the set of electrodes;

a telemetry circuit; and a processor configured to select one electrode combination of the predetermined subset of electrode combinations based on the received output and the map, and provide the selected electrode combination to a stimulation device coupled to the set of electrodes via the telemetry circuit for application of electrical stimulation to the patient via the selected electrode combination.

13. The system of claim 12, wherein the output of the control device comprises directional information that reflects a direction of a manipulation of the directional controller, and the processor selects the electrode combination such that a direction of movement of paresthesia resulting from application of electrical stimulation via the selected electrode combination reflects the direction of the manipulation of the directional controller.

14. The system of claim 12, further comprising a memory configured to store a plurality of electrode combination maps, each of the electrode combination maps mapping the output of the control device to a respective predetermined subset of electrode combinations available from one of a plurality of electrode set configurations, wherein the processor is configured to receive information that describes a configuration of the set of electrodes coupled to the stimulation device and select the electrode combination map based on the configuration information.

15. The system of claim 12, wherein the processor is configured to select a plurality of electrode combinations and provide the selected electrode combinations to the stimulation device in response to the user manipulating the directional controller to test the plurality of electrode combinations by application of electrical stimulation from the stimulation device to the patient via the plurality of electrode combinations.

16. The system of claim 15, wherein the processor is further configured to identify one of the tested electrode combinations based on input received from the user via the control device and the input circuit, and recalibrate the map such that a center position of a manipulation range of the directional controller corresponds to the identified electrode combination.

17. The system of claim 15, wherein the map comprises amplitude scale factors associated with at least some of the electrode combinations, and the processor is configured to determine the amplitude scale factors based on paresthesia information received from the user during the testing via the input circuit.

18. The system of claim 15, wherein the processor is further configured to identify one of the tested electrode combinations based on input received from the user via the control device, and store the identified electrode combination within the memory for reapplication by the stimulation device at a later time.

19. The system of claim 12, wherein each of the predetermined subset of electrode combinations corresponds to a respective stimulation location.

20. The system of claim 19, wherein each of the predetermined subset of electrode combinations corresponds to a respective paresthesia location.

21. The system of claim 19, wherein the set of electrodes comprises a two dimensional array of electrodes, and the mapping of the subset of electrode combinations to the output of the control device in the electrode combination map enables the user to move the stimulation longitudinally and laterally.

22. A computer readable storage medium comprising instructions that cause a programmable processor to:

receive an output from the control device that reflects manipulation of a directional controller of the control device by a user;

select one electrode combination of a predetermined subset of electrode combinations based on the received output and an electrode combination map, wherein the electrode combination map maps the output of the control device to the predetermined subset of electrode combinations available from a set of electrodes implanted within a patient, wherein the electrode combinations specify polarities of electrodes of the set of electrodes; and provide the selected electrode combination to a stimulation device coupled to the set of electrodes for application of electrical stimulation to the patient via the selected electrode combination.

23. A mapping system comprising:
an input circuit configured to receive an output from a control device, the output reflecting manipulation of a directional controller of the control device by a user;
an electrode combination map that maps the output of the control device to a predetermined subset of electrode combinations available from a set of electrodes implanted within a patient, wherein the electrode combinations specify polarities of electrodes of the set of electrodes; and
a processor configured to select one of the subset of electrode combinations based on the received output and the map, and control a stimulation device coupled to the set of electrodes to apply electrical stimulation to the patient via the selected electrode combination.

* * * * *